(12) United States Patent
Trigiani

(10) Patent No.: US 6,710,363 B1
(45) Date of Patent: Mar. 23, 2004

(54) DETECTION LAMP EQUIPPED WITH LIGHT-EMITTING DIODE

(75) Inventor: Phil Trigiani, Mississauga (CA)

(73) Assignee: UView Ultraviolet Systems, Inc., Mississauga (CA)

(*) Notice: Subject to any disclaimer, the term of this patent is extended or adjusted under 35 U.S.C. 154(b) by 173 days.

(21) Appl. No.: 09/722,908

(22) Filed: Nov. 27, 2000

(51) Int. Cl.[7] .............................. G01J 1/00; G01M 3/04
(52) U.S. Cl. ........................ 250/504 H; 250/504 R; 250/455.11; 250/493.1; 250/302
(58) Field of Search ................... 250/493.1, 455.11, 250/504 R, 504 H, 302, 455.1

(56) References Cited

U.S. PATENT DOCUMENTS

| 5,608,213 A | * | 3/1997 | Pinkus et al. ............ 250/595.1 |
| 5,674,000 A | | 10/1997 | Kalley |
| 5,742,066 A | | 4/1998 | Cavestri |
| 5,788,364 A | | 8/1998 | Cooper et al. |
| 5,816,692 A | | 10/1998 | Cooper et al. |
| 5,905,268 A | | 5/1999 | Garcia et al. |
| 5,959,306 A | | 9/1999 | Kalley et al. |
| 6,136,612 A | * | 10/2000 | Ciana et al. ................. 436/546 |

FOREIGN PATENT DOCUMENTS

DE          19938480 A    *  3/2000

* cited by examiner

Primary Examiner—Nikita Wells
(74) Attorney, Agent, or Firm—Bell, Boyd & Lloyd LLC

(57) ABSTRACT

The present application reveals a lamp and a method for detecting leaks in air-conditioning and refrigeration systems. The lamp uses one or more light-emitting diodes (LEDs) as a light source to detect fluorescent dyes that have been added to the air-conditioning or refrigeration system.

14 Claims, 5 Drawing Sheets

SINGLE LED LIGHT

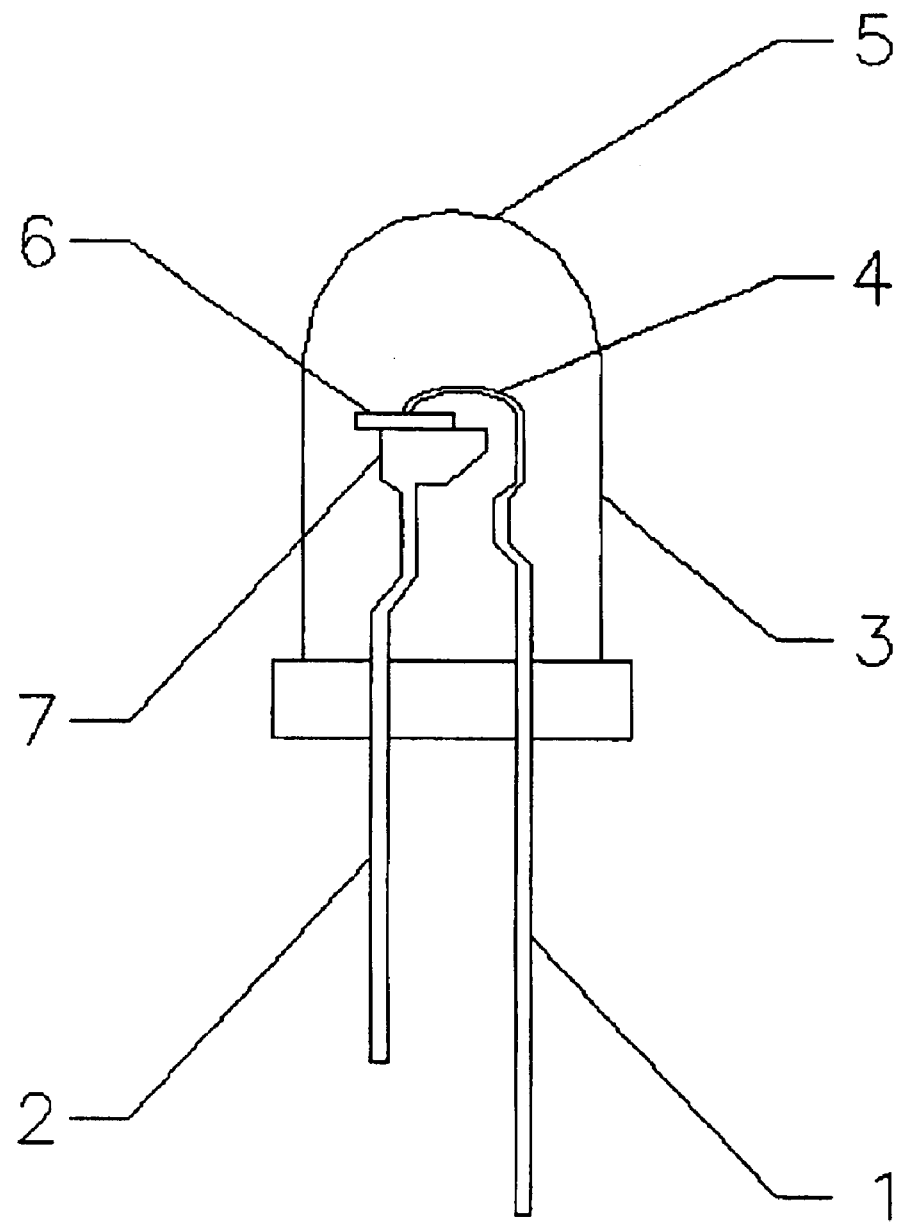
FIGURE 1: DETAILED LED

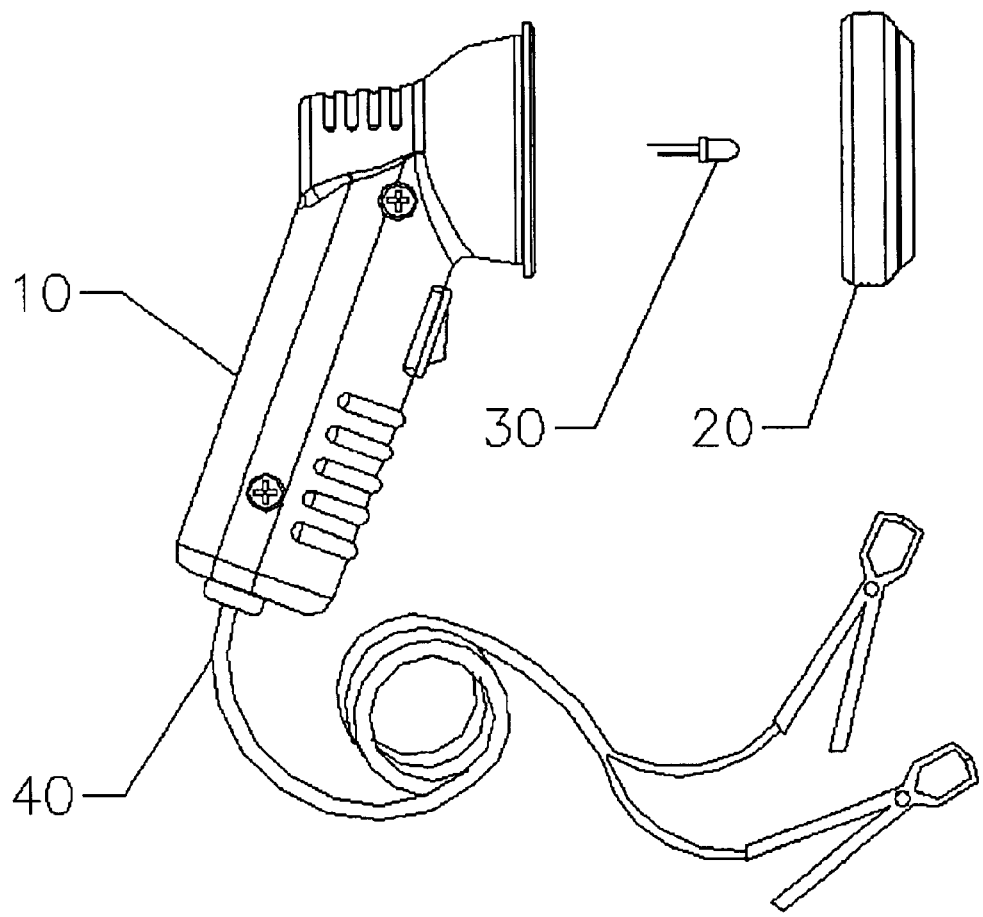
FIGURE 2: SINGLE LED LIGHT

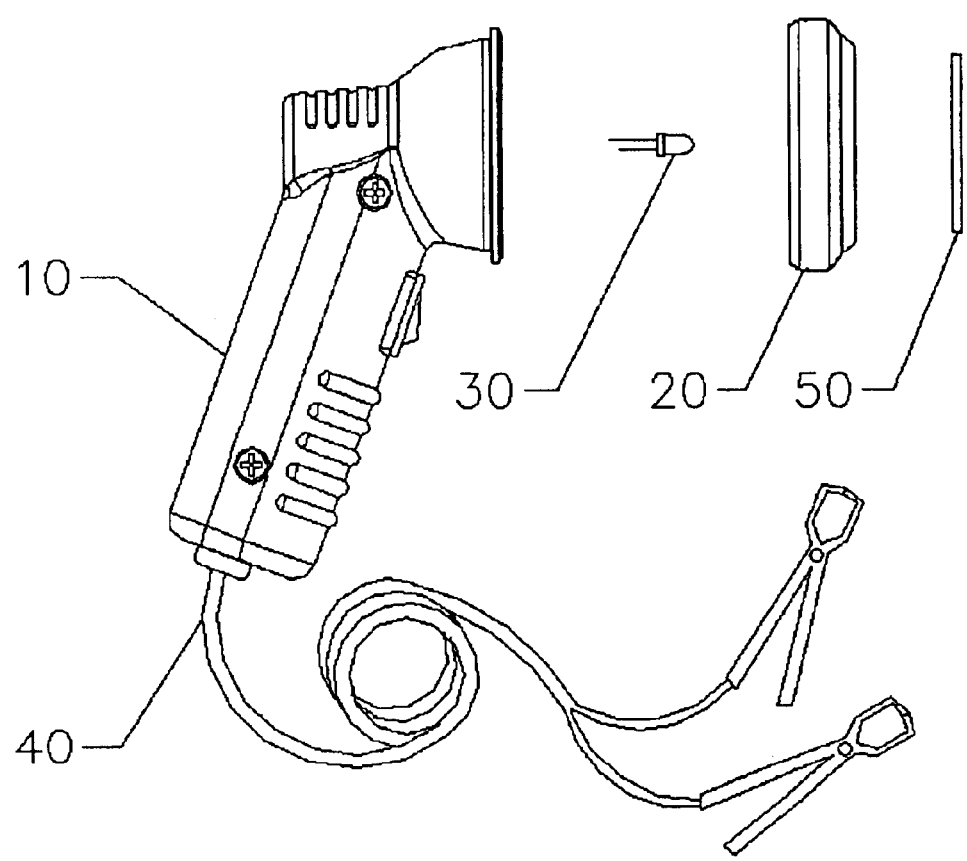
FIGURE 3: SINGLE LED LIGHT WITH LENS

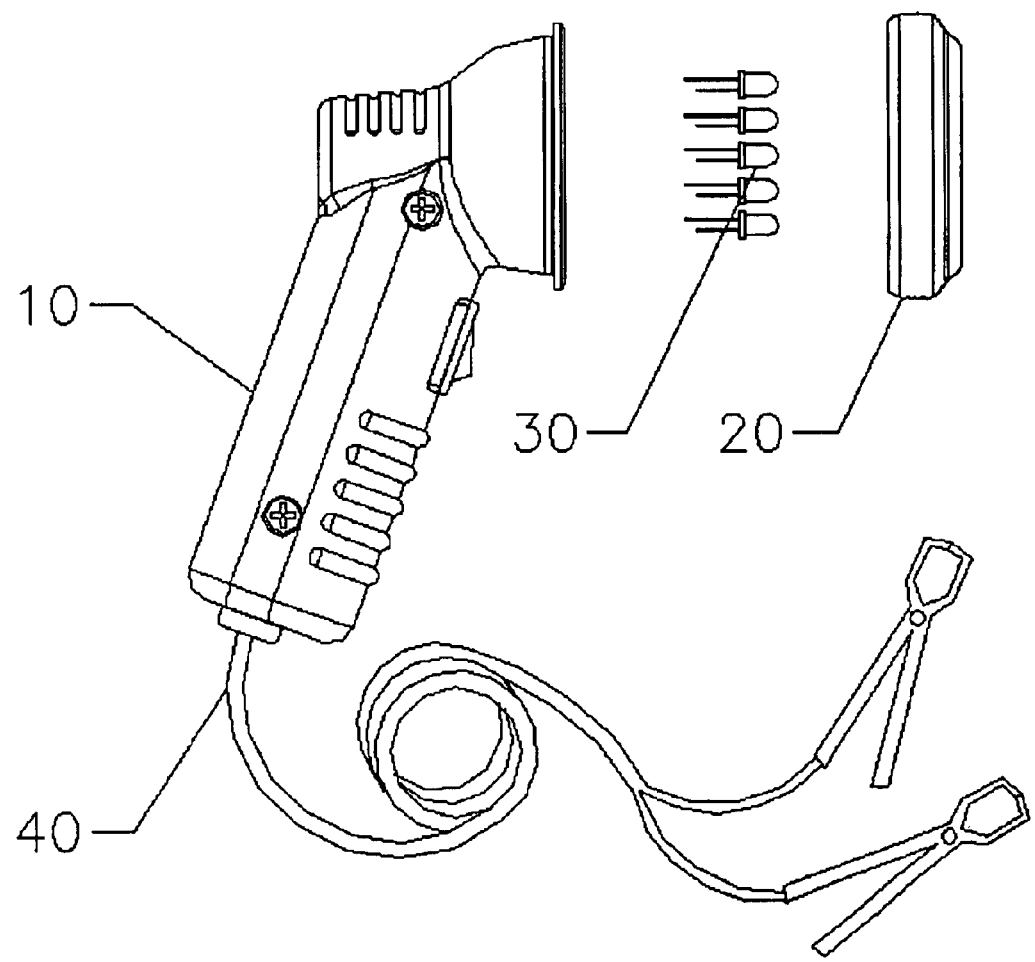
FIGURE 4: MULTIPLE LED LIGHT

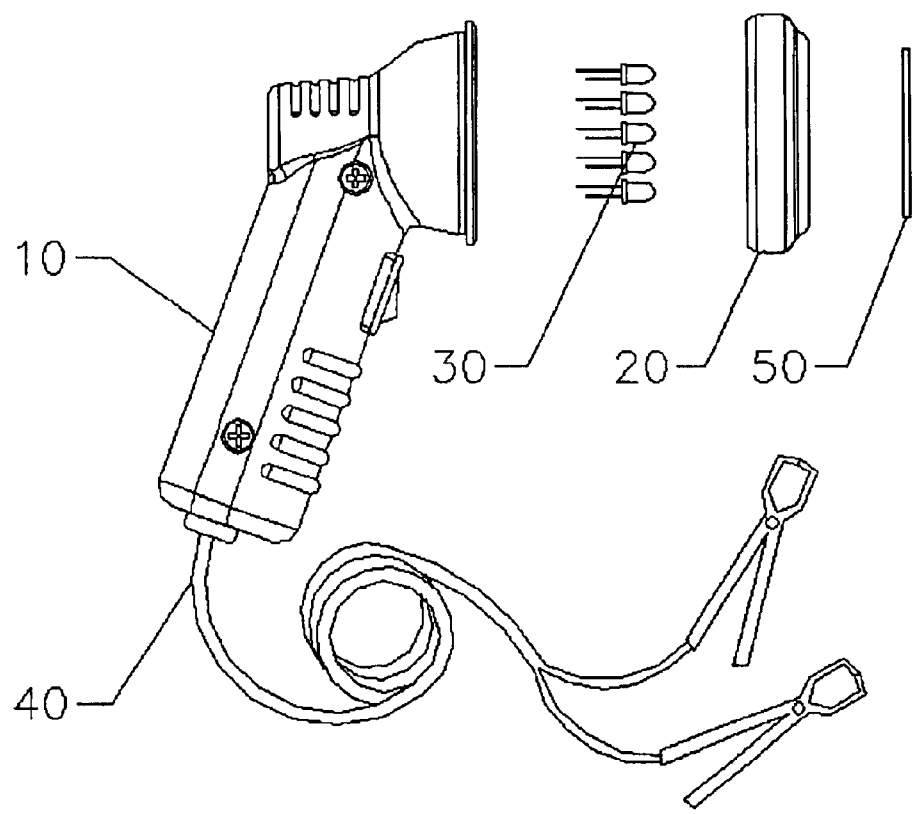
FIGURE 5: MULTIPLE LED LIGHT WITH LENS

DETECTION LAMP EQUIPPED WITH LIGHT-EMITTING DIODE

BACKGROUND OF THE INVENTION

1. Field of the Invention

The present application is for a lamp for detecting leaks in commercial and industrial air-conditioning and refrigeration systems and other liquid recirculating systems such as those emloying engine oil, transmission fluid and hydraulic fluid. The lamp uses a light-emitting diode (LED) as a light source to detect fluorescent dyes that have been added to the air-conditioning or refrigeration system.

2. Description of the Related Art

Leak detection, materials detection and qualitative non-destructive testing are well suited to techniques employing fluorescence detection. These techniques rely upon the unique physical property of various materials to fluoresce when excited by certain wavelengths of visible or ultraviolet (UV) light.

It is a well-known phenomenon that electromagnetic energy within the near ultraviolet spectrum of approximately 315 to 400 nanometer wavelengths produces fluorescence in certain materials, e.g., fluorescent dyes. These fluorescent materials absorb radiated energy at the near UV wavelengths and re-radiate or emit it at a longer wavelength in the visible spectrum. Thus, when fluorescent material absorbs electromagnetic energy in a specific excitation frequency band in a specific wavelength range, the material can emit electromagnetic energy in a characteristic fluorescent emission frequency band within the visible light spectrum. This phenomenon has enabled inspection and detection techniques in which fluorescent dyes, inks or pigments are illuminated by lamps selectively filtered to emit only ultraviolet (invisible to the human eye) and then re-radiate with a high luminescence in the visible spectrum. Some newer fluorescent dyes respond well to higher wavelengths of light in the visible violet and blue range in addition to the invisible UV range.

For example, the slow leakage of refrigerant from an air conditioning system is difficult to locate by any other means. The reason for the difficulty is because the refrigerant escapes as an invisible gas at such a low rate and rapid diffusion that the concentration of refrigerant in air near the leak site is difficult to differentiate from that surrounding any other location along the system circulation lines. However, by adding into the circulating system a small amount of fluorescent dye that is soluble in the refrigerant, the dye is carried out of the system with the refrigerant and glows brightly at the leak site when the area is swept with a UV lamp.

A similar procedure can be used to locate leaks of other fluids, such as lubricants, oils, fuels, heat transfer fluids or hydraulic fluids. Other UV inspection techniques use fluorescent-dyes or paint to detect fissures or stress cracks in structural members.

Conventional inspection lamps employ high intensity light sources (incandescent bulbs) operating at high temperatures to generate a sufficient photon flux for detection applications and utilize filters to absorb the undesirable wavelengths. These bulbs give off light owing to their temperature (incandescence). The power of the lamps is very high in wattage and therefore the lamp produces heat. A black light filter can be used but the filter is very restrictive and allows only UV wavelengths to be transmitted while all of the remaining wavelengths are absorbed. These filters typically have a transmission efficiency of 50–70% for the UV wavelengths (320–380 nm). To compensate for the limited transmission efficiency, the power of the lamps is very high in wattage and therefore heat producing. These lamps are usually 20–150 watts. Consequently, the life expectancy of the bulb is limited.

The fluorescent dyes used in this system typically have maximum excitation in the range of 320–380 nm. Some newer dyes respond well to higher wavelengths of light in the visible violet and blue range in addition to the invisible UV range (340–440 nm). With these dyes, improved photographic-type blue filters are used with smaller, low wattage lamps. These blue filters work well in lamps of 50 watts or less. At 50 watts, the lamps do not produce as much heat and although the blue filter allows some visible light to be transmitted, the dyes are still acceptably excited. In most cases, the lamps using these blue filters are also sold with special glasses (blue blocker glasses) that block the visible blue spectrum light transmitted through the blue filters. These glasses assist the operator in finding the leaks and seeing the dye reaction to UV, blue and violet light. In addition, these blue filters are much more prone to temperature damage and cracking than the black light filters. However, the transmission efficiency is greater by about 10% as compared to that for the black light filters. Also, the blue filters and the blue blocker glasses make the dye more visible to the technician.

Newer improved filters have been developed by applying a dielectric coating, that does not effect the visible and lower spectrum of light transmission, to a piece of glass. Such filters are referred to as dielectric or dichroic filters. These terms are interchangeable. Dielectric refers to the process used, and dichroic is the type of coating applied, also known as thin-film coating. For example, dichroic filters with a dielectric coating have been developed in the entertainment industry and have high levels of transmission. The dichroic filter with a dielectric coating allows UV, blue and IR wavelengths to be transmitted while most visible wavelengths are blocked. Thus, this type of filter does not absorb the IR heat and has a transmission efficiency of over 90% for the desired wavelengths. These advantages allow users to reduce the size and wattage of the detection lamps.

Luminescence, on the other hand, is the result of electronic excitation of a material. The light-emitting diode (LED) is a p-n junction in which an applied voltage yields a flow of current, and the recombination of the carriers injected across the junction results in the emission of light. The process involved here is in effect electroluminescence. The ratio of the number of emitted photons to the number of electrons crossing the p-n junction is the quantum efficiency. LED emission is generally in the visible part of the spectrum with wavelengths from 400 nm to 700 nm or in the near infrared with wavelengths between 700 and 2000 nm.

Red, yellow and green light-emitting diodes are known. More than 20 billion LEDs are produced each year. Visible LEDs are used as numeric displays or indicator lamps and are sufficiently bright that a row of red LEDs are used in an automobile spoiler to replace the conventional rear-window brake light. Infrared LEDs are employed in optoisolators, ink television remote controls, and as sources in optical communication systems. The applied voltage is near 2.0 volts. The current depends on the application and ranges from a few milliamperes to several hundred milliamperes. Thus, LEDs function with low power drain, at reduced temperatures and have an extremely long life expectancy, e.g., five to ten years or more, as compared to incandescent bulbs.

The present application reveals a lamp for detecting fluorescent dyes in an air-conditioning or refrigeration system. The lamp uses a light-emitting diode as a light source rather than conventional UV-emitting light sources. Consequently, the lamp operates with low power drain, at reduced temperatures and has an extremely long life expectancy as compared to conventional detection lamps equipped with incandescent bulbs.

SUMMARY OF THE INVENTION

The present application discloses a lamp and a method for detecting fluorescent dyes that have been added to an air conditioning or refrigeration system, where the fluorescent dyes reemit light at a wavelength greater than the wavelength of light emitted from the lamp. The lamp comprises a lamp housing, at least one light-emitting diode within the lamp housing and means for providing power to the lamp, where the light emitted from the lamp is restricted to a predetermined range effective to enhance the reemission of light from the fluorescent dyes.

In preferred embodiments of the lamp, the diode is a blue light-emitting diode or a UV light-emitting diode and the blue light-emitting diode is an indium gallium nitride semiconductor. In other preferred embodiments, the blue light-emitting diode is a laser diode and the laser diode is a gallium nitride based laser diode.

In yet other preferred embodiments, the lamp further comprises a protector ring connected to the lamp housing and a lens positioned within the protector ring. The lens can be a filter selected from the group consisting of black, red, amber, yellow, green, blue, indigo, violet, UV light and full spectrum filters. In other preferred embodiments, the lens is a dichroic filter and the lamp further comprises a blocker glass.

In more preferred embodiments, the lamp further comprises a plurality of light-emitting diodes and each of the light-emitting diodes emits the same color light.

The present application also discloses a method for detecting leaks in an air-conditioning or refrigeration system. The method comprises the steps of inserting a fluorescent dye into an air-conditioning or refrigeration system, running or operating the air-conditioning or refrigeration system and inspecting the air-conditioning or refrigeration system with a lamp comprised of housing, at least one light-emitting diode within the lamp housing and means for providing power to the lamp.

BRIEF DESCRIPTION OF THE DRAWINGS

FIG. 1 is a schematic representation of a light-emitting diode.

FIG. 2 shows an embodiment of the detection lamp of the present invention equipped with a single LED light source.

FIG. 3 shows an embodiment of the detection lamp of the present invention equipped with a single LED light source and a lens.

FIG. 4 shows an embodiment of the detection lamp of the present invention equipped with multiple LED light sources.

FIG. 5 shows an embodiment of the detection lamp of the present invention equipped with multiple LED light sources and a lens.

DETAILED DESCRIPTION

The present invention is for a lamp and a method for detecting leaks in an air-conditioning or refrigeration system. The lamp uses a light-emitting diode (LED) as a light source for detecting a fluorescent dye that has been added to the air-conditioning or refrigeration system.

FIG. 1 shows a light-emitting diode. Power is applied to one side of the LED semiconductor through a positive power lead or anode 1 and a whisker 4. The other side of the semiconductor is attached to the top of an anvil 7 that is the negative power lead or cathode 2. It is the chemical makeup of the LED semiconductor 6 that determines the color of the light the LED produces.

Semiconductors can be made of, for example, gallium arsenide, GaAs; gallium arsenide phosphide, $GaAs_{1-x}P_x$; aluminum gallium arsenide, $Al_xGa_{1-x}As$; aluminum gallium indium phosphide, $(Al_xGa_{1-x})_yIn_{1-y}P$; gallium indium arsenide phosphide, $Ga_xIn_{1-x}As_yP_{1-y}$, etc. LEDs can be used to produce infrared, red, amber, yellow, green, blue, indigo, violet, ultraviolet or even white light. White light is a combination of red, green and blue light. Presently, it is possible to produce white light with a single LED using a phosphor layer (yttrium aluminum garnet) on the surface of a blue (gallium nitride) chip. The blue light-emitting diode is preferred and uses an indium gallium nitride (InGaN) semiconductor 6.

A high impact plastic or epoxy resin enclosure 3 surrounds the semiconductor 6 and has two main functions. It is designed to allow the most light to escape from the semiconductor and it protects the LED semiconductor from the surrounding environment. A lens 5 focuses the light (view angle) escaping from the semiconductor. The entire unit is totally embedded in epoxy. This makes the LED virtually indestructible. There are no loose or moving parts within the solid epoxy enclosure. Therefore, the light-emitting diode is essentially a p-n junction semiconductor diode that emits light when current is applied. By definition, it is a solid-state device that controls current without heated filaments and is thus very reliable.

The light-emitting diodes of the present invention include laser diodes. These laser diodes produce a narrower spectrum of light than conventional LEDs. For example, Toshiba (Japan) has developed a gallium nitride (GaN) based blue diode that emits light at a wavelength of 417 nm. This laser diode is comprised of ultra-thin layers of indium gallium nitride (InGaN). Nichia Chemical Industrial Co, Ltd. (Japan) has developed a laser diode that emits light in the violet spectrum. This laser diode uses a sapphire substrate. First, a 100 micron-thick gallium nitride (GaN) layer is formed on the sapphire substrate and then the sapphire substrate is removed by polishing to leave an 80 micron-thick GaN substrate.

FIG. 2 shows an embodiment of the detection lamp of the present invention equipped with a single LED. The detection lamp is comprised of a lamp housing 10, a protector ring or cap 20, a single light-emitting diode 30 within the lamp housing and a cable 40 for connection to a power source. Obviously, the housing can have any shape provided that the light from the LED is emitted from the housing.

The detection lamp can function without the use of filters, thereby lowering the manufacturing cost. Since the size of the LED is considerably smaller than that of conventional incandescent bulbs, the detection lamp can be miniaturized, thereby facilitating maneuvering inside an engine compartment and around an air-conditioning system of an automobile. The inspection lamp equipped with an LED is extremely durable, drop resistant and impact resistant, in part, because of the construction of the LED, as described above. Also, the inspection lamp can be made waterproof which is a great advantage in an automotive service environment exposed to numerous liquids and solvents.

Furthermore, the inspection lamp uses a very low current. For example, it can be operated with 2–5 volts. The lamp can be powered by AC, DC or even solar power. Also, there is a constant output of light regardless of voltage. There is very little heat produced and this is extremely advantageous for a mechanic working around the exposed engine compartment of an automobile.

FIG. 3 shows an embodiment of the detection lamp of the present invention equipped with a single LED and a lens. The detection lamp is comprised of a lamp housing 10, a protector ring or cap 20, which also functions as a lens holder, a lens or filter 50, a single light-emitting diode 30 within the lamp housing and a cable 40 for connection to a power source.

The lens functions to block out undesirable wavelengths emitted from the LED and to transmit only the desired wavelengths. For example, a blue LED emitting at 430–470 nm can be-equipped with a filter blocking or reflecting wavelengths between 450–500 nm. Therefore, only wavelengths between 430–450 nm-will be transmitted from the lens. The lens may be selected from black light, blue light or any desired wavelength blocker or transmitter, even a full spectrum filter. Thus, dichroic filters may be used in the present invention. Furthermore, a blocker glass can be used in conjunction with the lens, e.g., a blue blocker glass can be used with a blue filter or lens. The choice of the filter will depend on the color emitted by the LED and the wavelength desired to be transmitted from the lamp.

The inspection lamp can be equipped with more than one LED, for example, 2, 5, 10, 25 or more, to increase the light output of the lamp. Typically, the life expectancy of the blue LED exceeds 100,000 hours.

FIG. 4 shows an embodiment of the detection lamp of the present invention equipped with multiple LEDs. The detection lamp is comprised of a lamp housing 10, a protector ring or cap 20, multiple light-emitting diodes 30 within the lamp housing and a cable 40 for connection to a power source.

In a preferred embodiment, each of the multiple light-emitting diodes emits the same color light. However, different color-emitting LEDs may be used in the same lamp. Thus, a red LED, a green LED and a blue LED can be used to generate white light in the lamp.

FIG. 5 shows an embodiment of the detection lamp of the present invention equipped with multiple LEDs and a lens. The detection lamp is comprised of a lamp housing 10, a protector ring or cap 20, which also functions as a lens holder, a lens or filter 50, multiple light-emitting diodes 30 within the lamp housing and a cable 40 for connection to a power source.

The following non-limiting examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain components may be substituted for the components described herein while the same or similar results would be achieved. All such similar substitutes and modifications apparent to those skilled in the art are deemed to be within the spirit, scope and concept of the invention as defined by the appended claims.

EXAMPLES

Example 1

7.5 ml of fluorescent dye (part no. 399006, UView Ultraviolet Systems, Inc., Mississauga, Ontario, Canada) were inserted into an automotive air-conditioning system of a 1999 Mercedes ML430. The dye fluoresces in the excitation range of 450–550 nm. The air-conditioning system was turned on and allowed to run for one minute. The air-conditioning system was inspected for leaks using an ultraviolet lamp equipped with a blue light-emitting diode. The lamp is shown in FIG. 2. The blue LED was purchased from Hosfelt Electronics (part no. 25–368, Steubenville, Ohio) and emitted blue light in the range of 450–600 nm. Within one minute of inspection, a leak was detected directly below the compressor and appropriate repairs made.

Example 2

7.5 ml of the same fluorescent dye used in Example 1 were inserted into an automotive air-conditioning system of a 2001 Chrysler PT Cruiser. The air-conditioning system was turned on and allowed to run for two minutes. The air-conditioning system was inspected for leaks using an ultraviolet lamp equipped with five blue light-emitting diodes. The lamp is shown in FIG. 4. The blue LEDs were purchased from Hosfelt Electronics (part no. 25–368, Steubenville, Ohio) and emitted blue light in the range of 450–600 nm. Within one minute of inspection, a leak was detected in a connection to the condenser and appropriate repairs made.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated by reference in their entirety and relied upon.

What is claimed is:

1. A miniaturized lamp for detecting fluorescent dyes that have been added to an air conditioning or refrigeration system, wherein the fluorescent dyes reemit light at a wavelength greater than the wavelength of light emitted from the lamp, the lamp comprising:

a) a lamp housing;

b) at least one light-emitting diode within the lamp housing; and c) means for providing power to the lamp, wherein the light emitted from the lamp is restricted to a predetermined range effective to enhance the reemission of light from the fluorescent dyes, and wherein said miniaturized lamp is sized to facilitate maneuvering inside an engine compartment and around an air-conditioning system or refrigeration system.

2. The lamp of claim 1, wherein the diode is a blue light-emitting diode.

3. The lamp of claim 1, wherein the diode is a UV light-emitting diode.

4. The lamp of claim 2, wherein the blue light-emitting diode is an indium gallium nitride semiconductor.

5. The lamp of claim 2, wherein the blue light-emitting diode is a laser diode.

6. The lamp of claim 5, wherein the laser diode is a gallium nitride based laser diode.

7. The lamp of claim 1, further comprising a protector ring connected to the lamp housing.

8. The lamp of claim 7, further comprising a lens positioned within the protector ring.

9. The lamp of claim 8, wherein the lens is a filter selected from the group consisting of black, red, amber, yellow, green, blue, indigo, violet, UV light and full spectrum filters.

10. The lamp of claim 9, further comprising a blocker glass.

11. The lamp of claim 9, wherein the lens is a dichroic filter.

12. The lamp of claim 1, further comprising a plurality of light-emitting diodes.

13. The lamp of claim 12, wherein each of the light-emitting diodes emits the same color light.

14. A method for detecting leaks in an air-conditioning or refrigeration system, comprising the steps of:

a) inserting a fluorescent dye into an air-conditioning or refrigeration system;

b) running the air-conditioning or refrigeration system; and c) inspecting the air-conditioning or refrigeration system with the lamp of claim 1.

* * * * *